(12) United States Patent
Shelton

(10) Patent No.: US 6,308,341 B1
(45) Date of Patent: Oct. 30, 2001

(54) TEMPERATURE AND COMPRESSION TREATMENT UNDERPANT

(75) Inventor: Sharon Rene Shelton, Huntsville, AL (US)

(73) Assignee: Reneé Shelton, Huntsville, AL (US)

(*) Notice: Subject to any disclaimer, the term of this patent is extended or adjusted under 35 U.S.C. 154(b) by 0 days.

(21) Appl. No.: 09/813,549

(22) Filed: Mar. 21, 2001

(51) Int. Cl.⁷ .................................................. A41D 1/00
(52) U.S. Cl. ........................................ 2/400; 2/403; 2/406
(58) Field of Search ................................ 2/400, 403, 408; 607/9, 108, 112, 114; 128/891, 379, 386, 898; 604/385–387, 358, 385.1, 389; 602/2, 60, 61, 67–71, 73

(56) References Cited

U.S. PATENT DOCUMENTS

| | | |
|---|---|---|
| 2,867,215 | * 1/1959 | Horton et al. ................. 128/379 |
| 3,809,096 | 5/1974 | York . |
| 5,167,655 | 12/1992 | McCoy . |
| 5,243,974 | * 9/1993 | Allen ............................. 607/108 |
| 5,277,180 | * 1/1994 | Angelillo et al. ............... 607/114 |
| 5,702,375 | * 12/1997 | Angelillo et al. ............... 604/358 |
| 5,716,319 | * 2/1998 | Sembert ........................... 600/38 |
| 5,935,595 | 8/1999 | Steen . |
| 6,048,327 | 4/2000 | Kieffer . |

* cited by examiner

Primary Examiner—Gloria M. Hale
(74) Attorney, Agent, or Firm—Lanier Ford Shaver & Payne P.C.; Gerald M. Walsh; David L. Berdan

(57) ABSTRACT

A temperature compression treatment underpant for providing therapy to the ano-genital region for relief of pain and discomfort, comprising a gel-pack with connecting straps at each end and an underpant with loops or other attachment means on the front and back external surfaces of the underpant. The gel-pack, cooled or heated to a desired temperature, is placed in the genital, perineal, and/or anal areas outside the underpant. One connecting strap is attached to the back external surface, the other connecting strap is pulled forward with as much tension as desired and attached to the front external surface, thereby providing temperature and compression treatment.

25 Claims, 2 Drawing Sheets

TEMPERATURE AND COMPRESSION TREATMENT UNDERPANT

BACKGROUND OF THE INVENTION

1. Field of the Invention

The present invention relates generally to a combination underpant and thermal treatment device for the application of cold or heat therapy and compression to the perineal, genital, and anal areas. More particularly, the present invention relates to an adjustable gel-pack which can apply both compression and thermal treatment to the perineal, genital, and/or anal areas.

2. Background of the Invention

The application of cold can offer an analgesic effect in the relief of pain and discomfort associated with surgery or other trauma to the perineal, genital, and/or anal areas. Gel-packs are known in the art and are used to provide cold therapy to the ano-genital region. These devices are usually placed directly on the traumatized area inside an underpant and do not provide compression. Compression of a gel-pack adjacent to the affected area can help reduce swelling and enhance the therapeutic effect of the cold therapy. The ability to apply the gel-pack therapy outside the underpant may be more comfortable and convenient for the user and/or the care giver. The present invention provides for the application of cold therapy and compression simultaneously outside the underpants as well as inside the underpant, as desired.

SUMMARY OF THE INVENTION

The present invention comprises an underpant and a gel-pack thermal device for providing compression and cold or heat therapy to the ano-genital region for the relief of pain and discomfort The present invention comprises an underpant and a gel-pack thermal device for providing compression and cold or heat therapy to the ano-genital region for the relief of pain and discomfort resulting from surgery, such as, for example, episiotomy, hemorrhoidectomy, prostate surgery, vasectomy, scrotal surgery, vulval surgery, or from child birth, or from any other trauma to the ano-genital region. The uniderpant has a waistband or belt that secures the underpant in place above the hips. There is a loop on the front and on the back of the underpant. The gel-pack has connecting straps, at least one extending from each end of the gel-pack. The gel-pack is placed as desired in the ano-genital region outside the underpant. The front connecting strap is passed through the loop on the front of the underpant and folded over to reversibly attach to itself. The back connecting strap is passed through the loop on the back of the underpant and folded over to reversibly attach to itself. The degree of compression applied by the gel-pack can be adjusted as desired by applying tension to the connecting straps prior to reversibly attaching teach connecting strap to itself.

An advantage of the present invention is that compression and heat or cold therapy can be applied simultaneously to the ano-genital region.

Another advantage of the present invention is that compression and heat or cold therapy can be applied outside the underpant.

Another advantage of the present invention is that the underpant is reversible and compression and heat or cold therapy can be applied inside the underpant.

Another advantage of the present invention is that it will relieve pain and discomfort of the ano-genital region resulting from surgery, child birth, or any other trauma.

Another advantage of the present invention is that it can be used to treat the genital, perineal. or anal regions selectively.

DETAILED DESCRIPTION OF THE PREFERRED EMBODIMENTS

While the following description details the preferred embodiments of the present invention, it is to be understood that the invention is not limited in its application to the details of construction and arrangement of parts illustrated in the accompanying drawings, since the invention is capable of other embodiments and of being practiced in various ways.

Figure 1:
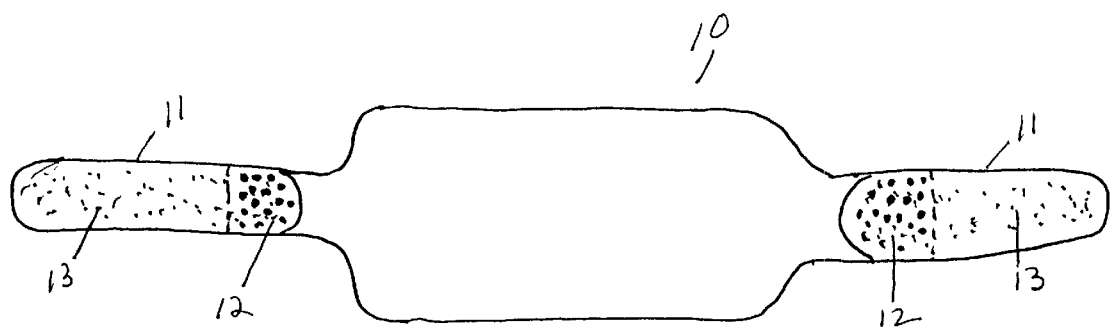
FIG. 1 shows a gel-pack with connecting straps on each end of the gel-pack, the connecting straps having hook and pile arrangements.

FIG. 1 shows a gel-pack 10 of the present invention having a connecting strap 11 on each end of the gel-pack. Connecting straps 11 have hook 12 and pile 13 arrangements so that connecting strap 1 can fold over and reversibly attach to itself.

Figure 2A:
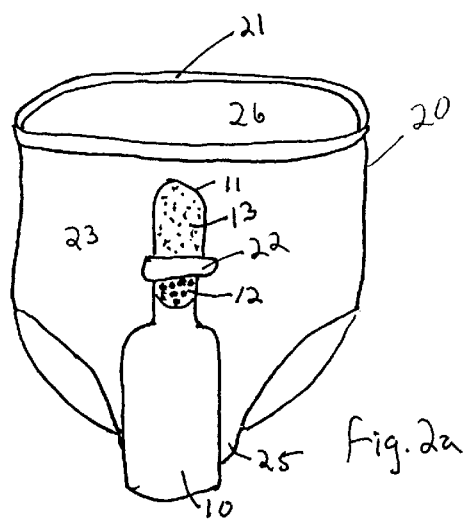
FIG. 2a shows a front view of an underpant with a gel-pack in place, and a connecting strap inserted through a loop on the front of the underpant.
Figure 2B:
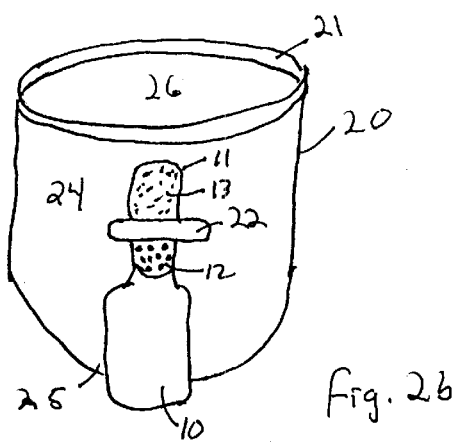
FIG. 2b shows a back view of an underpant with a gel-pack in place, and a connecting strap inserted through a loop on the back of the underpant.

FIGS. 2a and 2b show an underpant 20 of the present invention having a waist band 21 at the top of underpant 10, loops 22, a front external 23, a back external surface 24, and inside surface 26. FIGS. 2a and 2b show gel-pack 10 in place on the external bottom surface 25 of underpant 20 with connecting straps 11 inserted through loop 22 on front external 23 of underpant 20 (FIG. 2a) and through loop 22 on back side 24 (FIG. 2b).

Figure 3A:
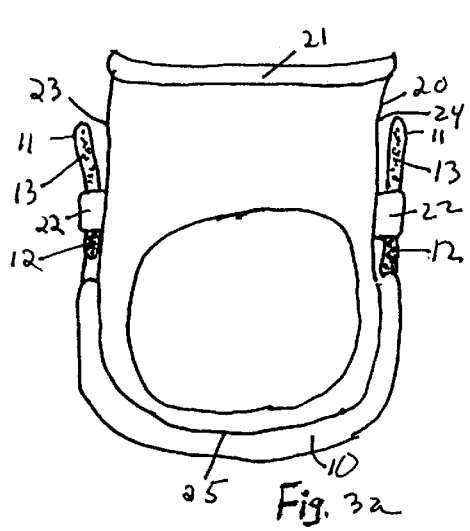
FIG. 3a shows a side view of an underpant with a gel-pack in place, and the connecting straps inserted through the loops on the front and back of the underpant.
Figure 3B:
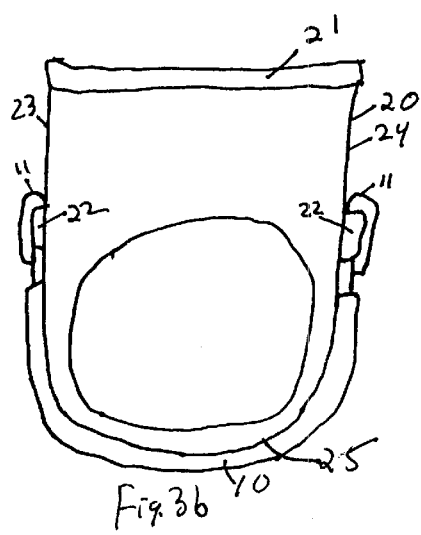
FIG. 3b is similar to FIG. 3a but shows the connecting strap folded over and reversibly attached to itself.

FIGS. 3a and 3b show a side view of underpant 20 with gel-pack 10 in place on the bottom external 25 of underpant 20 with connecting straps 11 inserted through loops 22 on front external 23 and back external surface 24 (FIG. 4a), and with each connecting strap 11 folded over loop 22 and reversibly attached to itself by hook 12 and pile 13 arrangements.

Figure 4A:
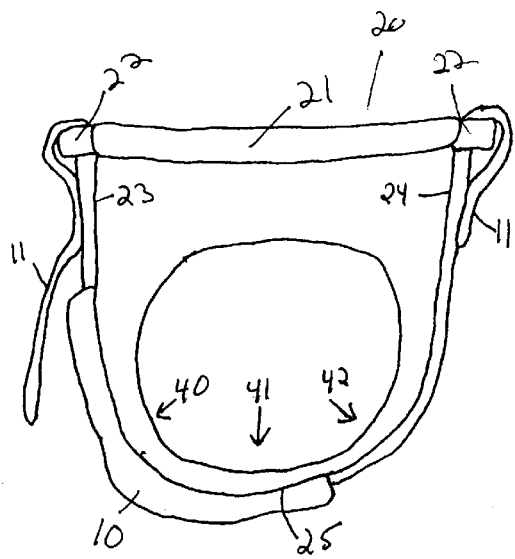
FIG. 4a and FIG. 4b show how the length of the gel-pack and/or its connecting straps can be varied so that the gel-pack can be positioned towards the front, middle, or back of the underpant as desired.
Figure 4B:
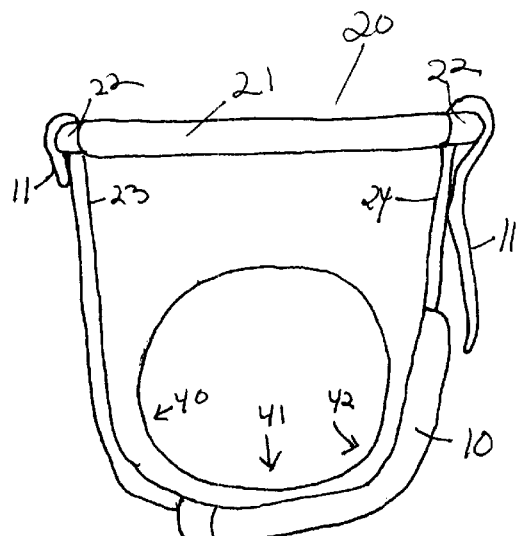

FIGS. 4a and 4b show how the length of the gel-pack 10 and/or its connecting straps 11 can be varied in length so that the gel-pack can be positioned, as desired, towards the front, bottom 25, or back 24 of the underpant 20. By placing the gel-pack 10 towards the front (FIG. 4a), middle, or back (FIG. 4b) of underpant 20, a user can apply thermal treatment and compression selectively to the genital 40, perineal 41, or anal areas 42, respectively. In addition, FIGS. 4a and 4b show that loops 22 can also be placed on waistband 21 on the front 23 or back 24 of underpant 20.

Figure 5A:
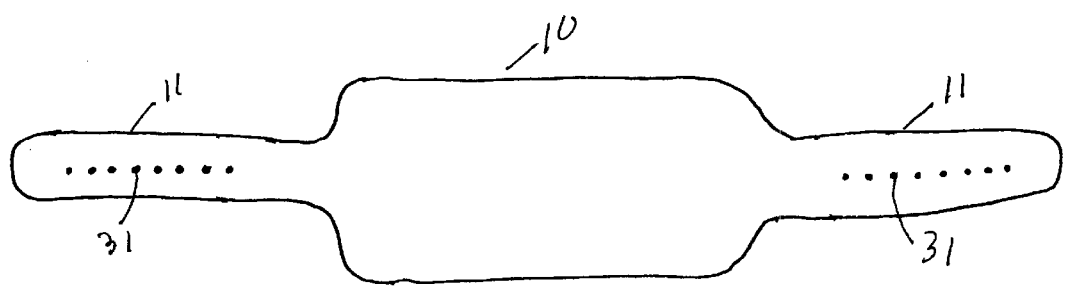
FIG. 5a shows an alternate embodiment of the gel-pack wherein the connecting straps have snaps.
Figure 5B:
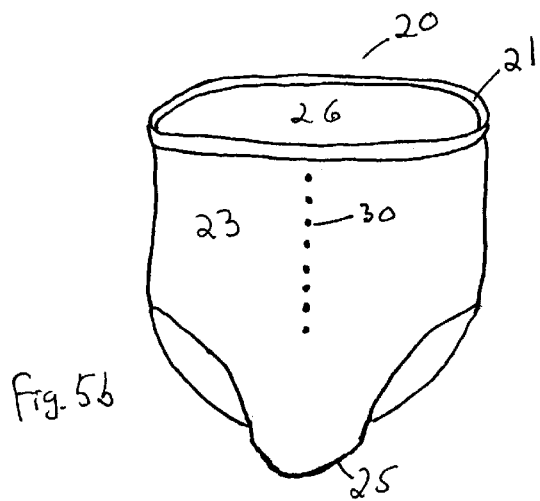
FIG. 5b shows an alternate embodiment of the underpant having snaps for reversible attachment to the connecting straps of the gel-pack.

FIGS. 5a and 5b show an alternate embodiment of the present invention. Instead of loops 22, underpant 20 has snaps 30 on front external surface 23 (FIG. 5b) and back external surface 24. Likewise connecting straps 11 on gel-pack 10 have reciprocating snaps 31 (FIG. 5a) so that connecting straps 11 are reversibly attached to front external surface 23 and back external surface 24 of underpant 20 by snaps 30.

The method of use of the temperature and compression treatment underpant of the present invention is described as follows. A user wears underpant 20 similar to conventional under pants. The gel-pack 10 is positioned in the crotch area as desired outside of underpant 10. Gel-pack 10 can cover the genital 40, perineal 41, or anal areas 42 individually or all of them simultaneously. On the other hand, gel-pack 10 can cover the genital 40 and perineal 41 areas only, or the perineal 41 and anal 42 areas only. This is accomplished by using a gel-pack of appropriate length and/or by moving the gel-pack 10 toward genital area 40 or toward anal area 42. Sustained compression is produced by reversibly attaching a connecting strap 11 to either front external surface 23 or back external surface 24 of underpant 10. The remaining strap 11 is then pulled toward the remaining unattached external surface of underpant 10 to create desired compression, and then reversibly attached to that remaining external surface to maintain that compression. For example, if a connecting strap is reversibly attached to the back external surface of the underpant, then the other connecting strap is pulled towards the front external surface under desired tension and then attached to the front external surface, and vice-versa. Waistband 21 secures underpant 20 above the hips and around the waist in an annular fashion sufficiently to bear the tension produced by gel-pack 10 and connection straps 11.

Any thermal device that is adapted to fit over the genital, perineal, or anal regions can be used in the present invention. The preferred thermal unit is a gel-pack well-known in the art for applying heat of cold to the body surface. Gel or reusable fluid materials employable in the gel-packs (pouches) of the present invention for heat exchange are well known in the art. For example, one reusable, heatable/chillable gel employable in the pouches could be composed of approximately 40% glycerine, 52% distilled water, and 8% starch. It is further well known in the art to provide plastic film pouches, packages, and containers and heating or refrigerating package constructions of plastic film material. Typical materials making up such films include polyethylene, cellophane, polypropylene, polyester, etc., and laminations thereof. The preferred gel-pack is reusable, can be heated in any suitable oven or heating device, including, preferably, a microwave oven, and can be placed in a freezer to cool the gel-pack to $0^B$ C. or lower without causing the gel to solidify.

The gel-pack of the present invention can be constructed in any suitable shape to cover the entire genital-perineal-anal region or just the individual genital, perineal, or anal regions. The length of the connecting straps may be made as desired so that the gel-pack may be moved forward towards the genital area or back towards the anal area (FIGS. 4a and 4b) and the connecting straps will be able to reversibly attach to the front and back external surfaces of the underpant.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the gel-pack may have two or more connecting straps at each end. There may be two or more loops on the front and back external surfaces of the underpant. The loops on the external surfaces may have connecting means, such as, for example, hook or pile arrangements or snaps so that the connecting straps are folded over the loop and reversibly attached to the loops. There may be one or more hook or pile arrangements on the front and back external surfaces of the underpant so that connecting traps reversibly attach directly to the front and back external surfaces. The waistband may further comprise an adjustable belt or tie arrangements so that the top of the underpant may be secured above the hips and around the waist in an annular fashion, with as much tension as desired, to further support the compression produced by the gel-pack and connecting straps. The underpant may be worn and used inside-out so that the gel-pack is inserted and reversibly attached on the interior of underpant so worn.

It will be understood that various changes in the details, materials, and arrangements of the parts which have been described and illustrated above in order to explain the nature of this invention may be made by those skilled in the art without departing from the principle and scope of the invention as recited in the following claims.

I claim:

1. A temperature and compression treatment underpant comprising:
   a) a thermal treatment device having a first end and a second opposite end, said ends each having one or more connecting straps;
   b) an underpant having an external surface, an inside surface, a front, a back, a top, and a bottom;
   c) said underpant having a waistband at said top;
   d) said thermal device being positioned at said bottom external surface of said underpant, and said connecting straps reversibly attached to said front and said back external surfaces of said underpant under tension, to provide sustained compression and/or heat or cold treatment to the genital, perineal, and/or anal regions of a user.

2. The temperature and compression treatment underpant of claim 1 wherein said thermal device is a gel-pack.

3. The temperature and compression treatment underpant of claim 1 wherein said underpant has one or more loops on said front external surface and on said back external surface, and said connecting straps are inserted through said loops and reversibly attach to themselves.

4. The temperature and compression treatment underpant of claim 3 wherein said connecting straps reversibly attach to themselves with hook and pile arrangements.

5. The temperature and compression treatment underpant of claim 1 wherein said underpant has one or more loops on said front external surface and on said back external surface, and said connecting straps are inserted through said loops and reversibly attach to said loops.

6. The temperature and compression treatment underpant of claim 5 wherein said connecting straps reversibly attach to said loops with hook and pile arrangements.

7. The temperature and compression treatment underpant of claim 1 wherein said connecting straps reversibly attach directly to said front and back external surfaces of said underpant with hook and pile arrangements.

8. The temperature and compression treatment underpant of claim 1 wherein said connecting strap reversibly attach directly to said front and back external surfaces of said underpant with snaps.

9. The temperature and compression treatment underpant of claim 3 wherein said loops are attached to said waistband.

10. The temperature and compression treatment underpant of claim 5 wherein said loops are attached to said waistband.

11. The temperature and compression treatment underpant of claim 1 wherein said waistband comprises an adjustable belt to provide as much tension as desired around the waist of a user.

12. The temperature and compression treatment underpant of claim 1 wherein said underpant is turned inside-out so that said thermal treatment device is inserted and reversibly attached in the interior of said underpant so worn.

13. A temperature and compression treatment underpant comprising:
   a) a gel-pack for heat or cold treatment having a first end and a second opposite end, said ends each having one or more connecting straps;
   b) an underpant having an external surface, an inside surface, a front, a back, a top, and a bottom;
   c) said underpant having a waistband at said top and one or more loops on said front external surface and on said back external surface; and
   d) said gel-pack being positioned at said bottom external surface of said underpant, and said connecting straps being inserted through said loops under tension and reversibly attaching to themselves with a hook and pile arrangement to provide sustained compression and/or heat or cold treatment to the genital, perineal, and/or anal regions of a user.

14. A temperature and compression treatment underpant of claim 13 wherein said loops are attached to said waistband.

15. A temperature and compression treatment underpant of claim 13 wherein said waistband comprises an adjustable belt to provide as much tension as desired around the waist of a user.

16. A temperature and compression treatment underpant of claim 13 wherein said underpant is turned inside-out so that said gel-pack is inserted and reversibly attached in the interior of said underpant so worn.

17. A method of treating the genital, perineal, and/or anal regions of a user for relief of pain and discomfort, comprising:
   a) providing a temperature and compression treatment underpant according to claim 1, said underpant having a front external surface, a back external surface, a top, a bottom, a waistband at said top, a gel-pack having one or more connecting straps at a first end and one or more connecting straps at a second opposite end;
   b) wearing said underpant in a conventional manner with said waistband around the waist and above the hips of the user;
   c) heating or cooling said gel-pack to a desired temperature;
   d) placing said gel-pack in the area of the genital, perineal, and/or anal regions as desired at the bottom external surface of said underpant; and
   e) reversibly attaching said connecting strap on said first end to said back external surface of said underpant and reversibly attaching said connecting strap on said second end of said gel-pack to said front external surface under as much tension as desired by pulling said connecting strap on said second end towards said front external surface before reversibly attaching said connecting strap to said front external surface of said underpant, thereby providing sustained compression and/or heat or cold treatment to the genital, perineal, and/or anal regions of the user.

18. The method of claim 17 wherein said front and back external surfaces each have one or more loops and said connecting straps are reversibly attached to said front and back external surfaces by inserting said connecting straps through said loops and reversibly attaching each connecting strap to itself.

19. The method of claim 18 wherein said connecting strap is connected to itself by a hook and pile arrangement.

20. The method of claim 17 wherein said connecting straps are reversibly attached directly to said front and back external surfaces by a hook and pile arrangement.

21. The method of claim 17 wherein said connecting straps are reversibly attached directly to said front and back external surfaces by a snap arrangement.

22. The method of claim 18 wherein said loops are attached to said waistband.

23. The method of claim 17 wherein said waistband comprises an adjustable belt to provide as much tension as desired around the waist of the user.

24. The method of claim 17 wherein said underpant is turned inside-out so that said thermal treatment device is inserted and reversibly attached in the interior of said underpant so worn.

25. The method of claim 17 wherein said connecting strap on said first end is reversibly attached to said front external surface and said connecting strap on said second end is attached to said back external surface under as much tension as desired by pulling said connecting strap on said second end towards said back external surface before reversibly attaching said connecting strap to said back external surface.

* * * * *